(12) United States Patent
Hoffman et al.

(10) Patent No.: US 10,546,265 B2
(45) Date of Patent: Jan. 28, 2020

(54) MAIL MANIFEST SYSTEMS AND METHODS

(71) Applicant: Express Scripts Strategic Development, Inc., St. Louis, MO (US)

(72) Inventors: Robert E. Hoffman, Linden, IN (US); Jonathan W. Joplin, Chesterfield, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

(21) Appl. No.: 16/408,993

(22) Filed: May 10, 2019

(65) Prior Publication Data

US 2019/0266551 A1    Aug. 29, 2019

Related U.S. Application Data

(63) Continuation of application No. 15/358,260, filed on Nov. 22, 2016, now Pat. No. 10,332,061.

(51) Int. Cl.
| | |
|---|---|
| G06F 7/00 | (2006.01) |
| G06Q 10/08 | (2012.01) |
| B65G 1/00 | (2006.01) |
| G16H 20/13 | (2018.01) |

(52) U.S. Cl.
CPC .......... *G06Q 10/083* (2013.01); *B65G 1/00* (2013.01); *G16H 20/13* (2018.01)

(58) Field of Classification Search
None
See application file for complete search history.

(56) References Cited

U.S. PATENT DOCUMENTS

| | | | |
|---|---|---|---|
| 5,660,305 A | 8/1997 | Lasher et al. | |
| 5,720,154 A | 2/1998 | Lasher et al. | |
| 5,771,657 A | 6/1998 | Lasher et al. | |
| 6,892,512 B2 | 5/2005 | Rice et al. | |
| 7,185,477 B2 | 3/2007 | Rice et al. | |
| 7,765,776 B1* | 8/2010 | Leu .................. | B65B 5/045 |
| | | | 53/131.4 |
| 9,242,751 B1 | 1/2016 | Joplin et al. | |
| 2016/0023787 A1 | 1/2016 | Joplin | |
| 2016/0221762 A1* | 8/2016 | Schroader .......... | B65G 43/08 |
| 2016/0256898 A1* | 9/2016 | Alsop, Sr. .......... | B07C 7/04 |
| 2016/0263622 A1 | 9/2016 | El Bernoussi | |
| 2016/0332823 A1* | 11/2016 | Yang ................ | B65B 43/54 |
| 2017/0057751 A1 | 3/2017 | Fujihara et al. | |
| 2017/0312789 A1* | 11/2017 | Schroader .......... | B65G 43/10 |

* cited by examiner

Primary Examiner — Yolanda R Cumbess
(74) Attorney, Agent, or Firm — Dickinson Wright PLLC

(57) ABSTRACT

A pharmaceutical filling system for a high volume pharmacy is described. The system can include an outflow conveyor, and an injection conveyor to inject a package located thereon onto the outflow conveyor. The injection conveyor can be adjacent to the outflow conveyor and oriented substantially perpendicular to the outflow conveyor. The system can also include a monitoring system positioned to perform package monitoring of the outflow conveyor and to image the package on the outflow conveyor after the package has been injected onto the outflow conveyor. The monitoring system can be further configured to determine an intended destination of the package based on an identifier detected on the package in the image captured by the monitoring system. A routing device can be positioned to perform package routing of the package to an accumulation area for packages based on the determination of the intended destination of the package.

20 Claims, 10 Drawing Sheets

MAIL MANIFEST SYSTEMS AND METHODS

CROSS-REFERENCE TO RELATED APPLICATIONS

This application is a continuation application of U.S. patent application Ser. No. 15/358,260 filed on Nov. 22, 2016 which is incorporated by reference in its entirety.

FIELD

The present disclosure relates generally to the technical field of automated filling centers. In a specific example, the present disclosure may relate to a high volume fulfillment center (e.g., a high volume pharmacy, etc.) and to systems and methods for mail manifest, which may include devices for verifying and routing packaged orders for shipment.

BACKGROUND

A pharmacy may process and fill a large number of prescriptions and prescription orders. Automated systems may be used by a high volume pharmacy to process and fulfill prescriptions.

Frequently, more than one prescription drug is required to complete a prescription order. Portions of the prescription order may be fulfilled in different areas of the high-volume pharmacy. After fulfillment, the fulfilled prescriptions may be gathered into a complete prescription order for shipping.

BRIEF DESCRIPTION OF THE DRAWINGS

In the drawings, reference numbers may be reused to identify similar and/or identical elements.

DETAILED DESCRIPTION

Example systems and methods for mail manifest, for example, in a pharmacy, are described. In the following description, for purposes of explanation, numerous specific details are set forth in order to provide a thorough understanding of example embodiments. It will be evident, however, to one of ordinary skill in the art that these embodiments may be practiced without these specific details.

Generally, a prescription order is generated for a high volume pharmacy. The prescription order may include one or more than one prescription drug for fulfillment. Each prescription drug in a prescription order is an order component of the prescription order. Generally, the order components are pill bottles, liquid bottles, blister packs, unit-of-use packs, injectable package, spray bottles, tubes, ampoules, drop counters, insulated boxes, child-resistant containers, or other packaging having a quantity of a prescription drug contained therein.

Upon receipt of prescription orders by the pharmacy, a prescription order may be selected for fulfillment from among the received prescription orders. Some or all of the components of the selected prescription order may be fulfilled manually. Alternatively, some or all of the components of the selected prescription order may be fulfilled by an automated fulfillment device at the pharmacy. Once all components of the selected prescription order are fulfilled, the components may all be married up with one another either manually, automatically, or a combination of both. The assembled order components may be packaged for shipment, along with any other materials such as instruction materials. Prior to shipment, packaged orders may be verified, sorted, and organized through mail manifest machinery to optimize shipment.

Figure 1:
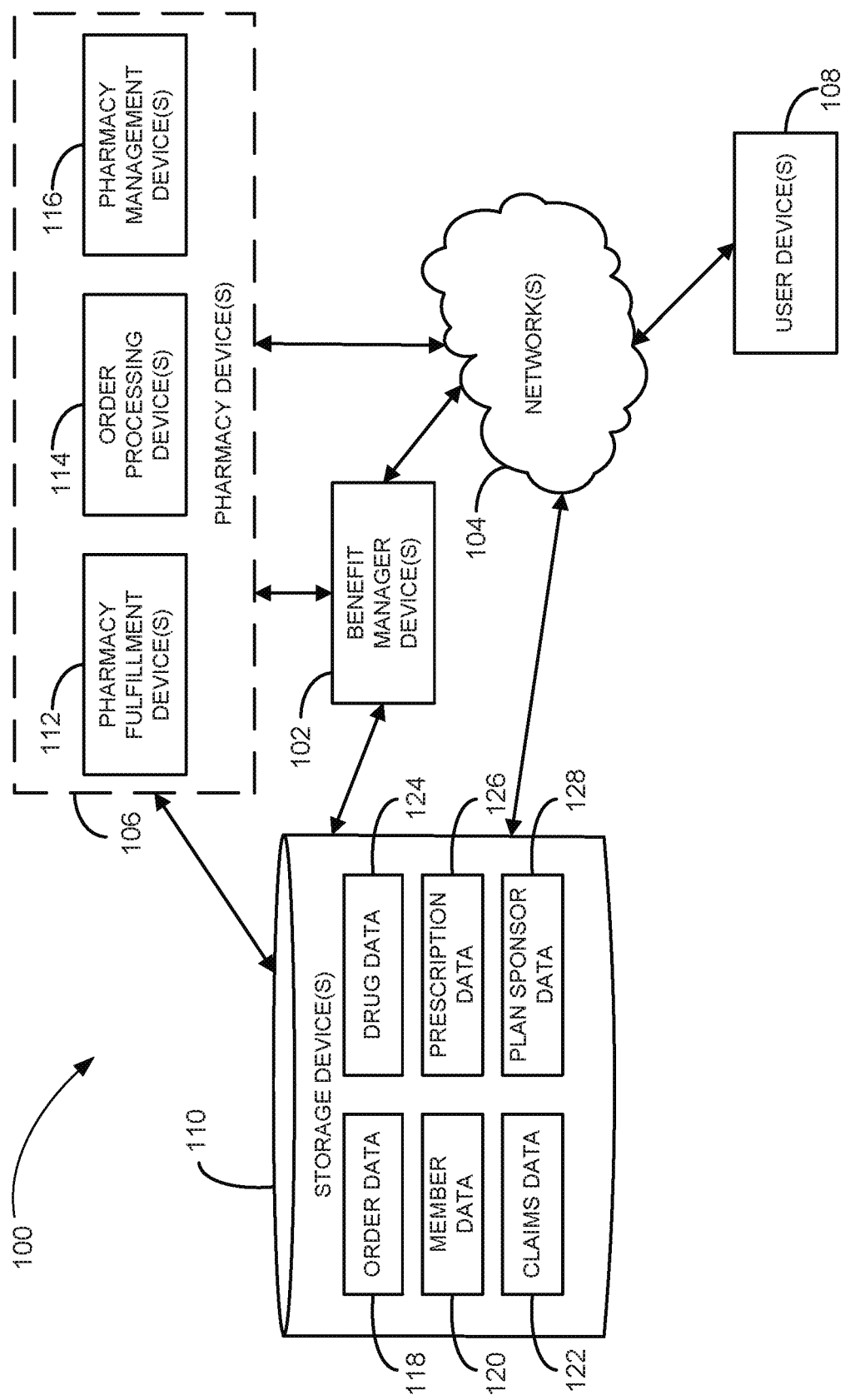
FIG. 1 is a diagram of an example implementation of a system for a high volume pharmacy, according to an example embodiment.

FIG. 1 is a block diagram of an example implementation of a system 100, according to an example embodiment. While the system 100 is generally described as being deployed in a high volume pharmacy or fulfillment center (e.g., a mail order pharmacy, a direct delivery pharmacy, an automated pharmacy, multiple package delivery center, and the like), the system 100 and/or components thereof may otherwise be deployed (e.g., in a lower volume pharmacy). A high volume pharmacy may be a pharmacy that is capable of filling prescriptions automatically, mechanically, manually, or a combination thereof. The system 100 may include a benefit manager device 102, a pharmacy device 106, and a user device 108, which may communicate with each other directly and/or over a network 104. The system 100 may also include a storage device 110.

The benefit manager device 102 is a device operated by an entity that is at least partially responsible for creation and/or management of the pharmacy or drug benefit. While such an entity operating the benefit manager device 102 is typically a pharmacy benefit manager (PBM), other entities may operate the benefit manager device 102 either on behalf of themselves, the PBM, another entity, or other entities. For example, the benefit manager device 102 may be operated by a health plan, a retail pharmacy chain, a drug wholesaler, a data analytics or other type of software-related company, or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmacies may be retail pharmacies, mail order pharmacies, specialty pharmacies, pharmaceutical vending machines or kiosks, and the like.

Some of the operations of the PBM that operates the benefit manager device 102 may include the following activities and processes. A member (or a person on behalf of the member) of a pharmacy benefit plan administered by or through the PBM attempts to obtain a prescription drug at a retail pharmacy location (e.g., a location of a physical store) from a pharmacist or a pharmacist technician. The member may also attempt to obtain the prescription drug through mail order drug delivery from a mail order pharmacy location, which may be the high volume pharmacy system 100. In some embodiments, the member may also attempt to obtain the prescription drug directly or indirectly through the use of a machine, such as a kiosk, vending unit, mobile electronic device, or a different type of mechanical, electrical, electronic communication device, and/or computing device. Such a machine may be filled with the prescription drug in prescription packaging, which may include multiple prescription components, by the high volume pharmacy system 100.

The member may have a copayment for the prescription drug that reflects an amount of money that the member is responsible to pay the pharmacy for the prescription drug. The money paid by the member to the pharmacy may come from personal funds of the member, a health savings account (HSA) of the member or the member's family, a health reimbursement arrangement (HRA) of the member or the member's family, a flexible spending account (FSA) of the member or the member's family, or the like. In some instances, an employer of the member may directly or indirectly fund or reimburse the member for the copayments.

The amount of the co-pay required from the member may vary with different pharmacy benefit plans having different plan sponsors or clients and/or prescription drugs. The member's copayment may be based a flat copayment (e.g., $10 or other dollar amounts), co-insurance (e.g., 10% or other percents), and/or a deductible (e.g., for first $500 of annual prescription drug expenses or other dollar amounts) for certain prescription drugs, certain types and/or classes of prescription drugs, and/or all prescription drugs. The copayment may be stored in the storage 110 or determined by the benefit manager device 102.

In some instances, the member may not pay the copayment or may only pay a portion of the copayment for the prescription drug. For example, if the usual and customary cost for a generic version of a prescription drug is $4, and the member's flat copayment is $20 for the prescription drug, the member may only be required to pay $4 to receive the prescription drug. In another example involving a worker's compensation claim, no copayment may be due by the member for the prescription drug.

In addition, copayments may also vary based on different delivery channels used for the prescription drug to be received by the member. For example, the copayment for receiving the prescription drug from a mail order pharmacy location may be less than the copayment for receiving the prescription drug from a retail pharmacy location.

In conjunction with receiving the copayment (if any) from the member and dispensing the prescription drug to the member, the pharmacy submits a claim to the PBM for the prescription drug. After receiving the PBM (e.g., through the benefit manager device 102) may perform certain adjudication operations including verifying eligibility for the member, identifying and/or reviewing an applicable formulary for the member to determine any appropriate copayment, coinsurance, and deductible for the prescription drug, and performing a drug utilization review (DUR) on the member. The PBM provides a response to the pharmacy (e.g. from the benefit manager device 102 to the pharmacy device 106) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated.

The aforementioned adjudication operations generally occur before the copayment is received and the prescription drug is dispensed. However, in some instances these operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be determined at least partially based on the type(s) of pharmacy network in which the pharmacy is included. Other factors may also be used to determine the amount in addition to the type of pharmacy network. For example, if the member pays the pharmacy for the prescription drug without using the prescription drug benefit provided by the PBM (e.g., by paying cash without use of the prescription drug benefit or by use of a so-called pharmacy discount card offering other negotiated rates), the amount of money paid by the member may be different than when the member uses the prescription or drug benefit. In some embodiments, the amount of money received by the pharmacy for dispensing the prescription drug and for the prescription drug itself may be higher than when the member uses the prescription or drug benefit. Some or all of the foregoing operations may be performed by executing instructions stored on the benefit manager device 102 and/or an additional device.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include an optical network. The network 104 may be a local area network or a global communication network, such as the Internet. In some embodiments, the network 104 may include a network dedicated to prescription orders, e.g., a prescribing network such as the electronic prescribing network operated by Surescripts of Arlington, Va.

Moreover, although the system shows a single network 104, multiple networks can be used. The multiple networks may communicate in series with each other to link the devices 102, 106-110 or in parallel to link the devices 102, 106-110.

The pharmacy device 106 may include an order processing device 114, a pharmacy management device 116, and a pharmacy fulfillment device 112 in communication with each other directly and/or over the network 104.

The order processing device 114 may receive information regarding filling prescriptions and may direct an order component to one or more than one of the devices of the pharmacy fulfillment device 112 at a pharmacy. The pharmacy fulfillment device 112 may fulfill, dispense, aggregate, and/or pack the order components of the prescription drugs in accordance with one or more than one of the prescription orders directed by the order processing device 114. The order processing device 114 may be deployed in the system 100, or may otherwise be used.

In general, the order processing device 114 is a device located within or otherwise associated with the pharmacy to enable fulfillment of a prescription and dispensing prescription drugs by the pharmacy fulfilment device 112. In some embodiments, the order processing device 114 may be an external device separate from the pharmacy and communicate with other devices located within the pharmacy.

For example, the external order processing device 114 may communicate with an internal order processing device 114 and/or other devices located within the system 100. In some embodiments, the external order processing device 114 may have limited functionality (e.g., as operated by a patient requesting fulfillment of a prescription drug), while the internal pharmacy order processing device 114 may have greater functionality (e.g., as operated by a pharmacist).

The order processing device 114 may track the prescription order as it is fulfilled by the pharmacy fulfillment device 112. The prescription order may include one or more than one prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a patient or a patient family. The order processing device 114 may also track and/or schedule literature or paperwork associated with each prescription order or multiple prescription orders that are being shipped together.

The pharmacy management device 116 may enable and/or facilitate management and operations in a pharmacy. For example, the pharmacy management device 116 may provide functionality to enable receipt and processing of prescription drug claims, management of pharmacy personnel, management of pharmaceutical and non-pharmaceutical products, track products in the pharmacy, record workplace incidents involve personnel and products, and the like. In some embodiments, the order processing device 114 may operate in combination with the pharmacy management device 116.

In some embodiments, the pharmacy management device 116 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy management device 116 may be utilized by the pharmacy to submit the claim to the PBM (e.g., through the benefit management device 102) for adjudication.

In some embodiments, the pharmacy management device 116 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some embodiments, the benefit manager 102 may track prescription drug fulfillment and/or other information for patients that are not members or have not identified themselves as members, at the time (or in conjunction with the time) in which they seek to have a prescription filled at a pharmacy.

The pharmacy fulfillment devices 112, the order processing device 114, and/or the pharmacy management device 116 may include circuitry, a processor, a memory to store data and instructions, and communication functionality. These devices 112-116, in some embodiments, are dedicated to performing processes, methods and/or instructions described herein. Other types of electronic devices specifically configured to implement with the processes, methods and/or instructions described herein may also be used.

In some embodiments, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (e.g., by utilizing a local storage) and/or through the network 104 (e.g., by utilizing a cloud configuration or software as a service. etc.) with the storage 110.

The user device 108 is used by a device operator. The device operator may be a user (e.g., an employee, a contractor, a benefit member, a patient of the pharmacy, or the like) associated with the system 100. Other device operators may also operate the user device 108. In some embodiments, the user device 108 may enable the device operator to attend to pharmacy operations in a convenient manner (e.g., remote from a pharmacy). In some embodiments, the user device 108 may enable the device operator to receive information about pharmacy processes, prescription drug fulfillment status, and the like.

The user device 108 may be a stand-alone device that solely provides at least some of the functionality of the methods and systems, or may be a multi-use device that has functionality outside of analysis of the methods and systems. Examples of the user device 108 include a set-top box (STB), a receiver card, a mobile telephone, a personal digital assistant (PDA), a display device, a portable gaming unit, a computing system, and the like. Other devices, however, may also be used. In some embodiments, the computing system may include a mobile computing device. For example, the user device 108 may include a mobile electronic device, such an iPhone or iPad by Apple, Inc., mobile electronic devices powered by Android by Google, Inc., and a Blackberry by Research In Motion Limited. The user device 108 may also include other computing devices, such as desktop computing devices, notebook computing devices, netbook computing devices, gaming devices, and the like. Other types of electronic devices may also be used.

The storage device 110 may include: a non-transitory storage (e.g., memory, hard disk, CD-ROM, and the like) in communication with the benefit manager device 102, the pharmacy device 106, and/or the user device 108 directly and/or over the network 104. The non-transitory storage may store order data 118, member 120, claims data 122, drug data 124, prescription data 126, and/or plan sponsor 128. Further, the system 100 may include additional devices, which may communicate with each other directly or over the network 104.

The order data 118 may be related to a prescription order. The order data may include the type of the prescription drug (e.g., drug name and strength) and quantity of the prescription drug. The order data 118 may also include data used for completion of the prescription, such as prescription materials and/or the type and/or size of container in which the drug is dispensed or in which is requested to be dispensed. In general, prescription materials include an electronic copy of information regarding the prescription drug for inclusion with or otherwise provided (e.g., via email) in conjunction with the fulfilled prescription. The prescription materials may include electronic information regarding drug interaction warnings, recommended usage, possible side effects, expiration date, date of prescribing, or the like. The order data 118 may be used by the pharmacy to fulfill a pharmacy order.

In some embodiments, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (e.g., a prescription bottle and sealing lid, prescription packaging, and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets, bins, trays, carts, and the like used to facilitate transportation of prescriptions within the pharmacy may also be stored as order data 118.

The member data 120 includes information regarding the members associated with the PBM. The information stored as member data 120 may include personal information, personal health information, protected health information, fitness data, health data, web and mobile app activity, and the like. Examples of the member data 120 include name, address, telephone number, e-mail address, prescription drug history, and the like. The member data 120 may include a plan sponsor identifier that identifies the plan sponsor associated with the member and/or a member identifier that identifies the member to the plan sponsor. The member data 120 may also include, by way of example, dispensation preferences such as type of label, type of cap, message preferences, language preferences, or the like.

The member data 120 may be accessed by various devices in the pharmacy to obtain information utilized for fulfillment and shipping of prescription orders. In some embodiments, an external order processing device 114 operated by or on behalf of a member may have access to at least a portion of the member data 120 for review, verification, or other purposes.

In some embodiments, the member data 120 may include information for persons who are patients of the pharmacy but are not members in a pharmacy benefit plan being provided by PBM. For example, these patients may obtain drug directly from the pharmacy, through a private label service offered by the pharmacy, or otherwise. In general, the use of the terms member (e.g., of a prescription drug benefit plan) and patient (e.g., of a pharmacy) may be used interchangeably in this disclosure.

The claims data 122 includes information regarding pharmacy claims adjudicated by the PBM under a drug benefit program provided by the PBM for one, or more than one, plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility, and the like. Additional information may be included.

In some embodiments, other types of claims beyond prescription drug claims may be stored in the claims data 122. For example, medical claims, dental claims, wellness claims, or other type of health care-related claims for members may be stored as a portion of the claims data 122.

In some embodiments, the claims data 122 includes claims that identify the members with whom the claims are associated. In some embodiments, the claims data 122 includes claims that have been de-identified (e.g., associated with a unique identifier but not with a particular, identifiable member), aggregated, and/or otherwise processed.

The drug data 124 may include drug name (e.g., technical name and/or common name), other names by which the drug is known by, active ingredients, an image of the drug (e.g., in pill form), and the like. The drug data 124 may include information associated with a single medication or multiple medications.

The prescription data 126 may include information regarding prescriptions that may be issued by prescribers on behalf of patients, who may be members of the pharmacy benefit plan, for example to be filled by a pharmacy. Examples of the prescription data 126 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, and the like.

Figure 2:
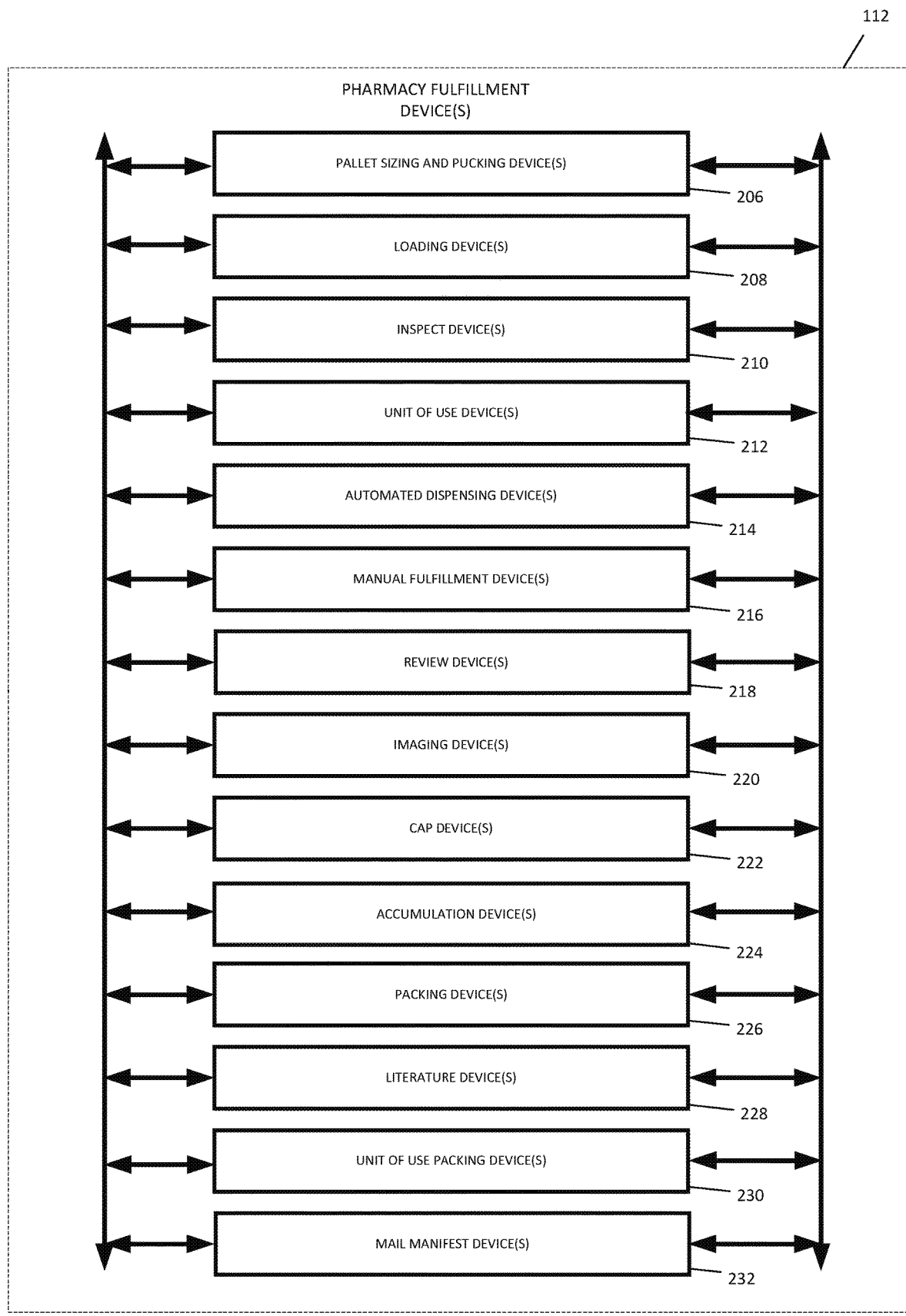
FIG. 2 is a block diagram of an example pharmacy fulfillment devices that may be deployed within the system of FIG. 1, according to an example embodiment.

FIG. 2 illustrates the pharmacy fulfillment device 112, according to an example embodiment. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the non-transitory storage 110, directly or over the network 104. Specifically, the pharmacy fulfillment device 112 may include pallet sizing and pucking device(s) 206; loading device(s) 208; inspect device(s) 210, unit of use device(s) 212, automated dispensing device(s) 214, manual fulfillment device(s) 214, review device(s) 218, imaging device(s) 220, cap device(s) 222, accumulation device(s) 224, literature device(s) 228, packing device(s) 226, unit of use packing device(s) 230, and mail manifest device(s) 232. Further, the pharmacy fulfillment device 112 may include additional devices, which may communicate with each other directly or over the network.

In some embodiments, operations performed by one or more of these devices 206-232 may be performed sequentially, or in parallel with the operations of other devices as may be coordinated by the order processing device 114. In some embodiments, the order processing device 114 tracks a prescription with the pharmacy based on operations performed by one or more than one of the devices 206-232.

In some embodiments, the pharmacy fulfillment device 112 may transport prescription drug containers, for example, between more than one of the devices 206-232 in the high volume fulfillment center, by use of pallets. The pallet sizing and pucking device 206 may configure pucks in a pallet. A pallet may be a transport structure for a number of prescription containers, and may include a number of cavities. A puck may be placed in one or more than one the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism, or the like. In one embodiment, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations, (e.g., at the high volume fulfillment center, or the like).

The inspect device 210 may verify that containers in a pallet are correctly labeled and in the correct spot on the pallet. The inspect device 210 may scan the label on one or more than one containers on the pallet. Labels of containers may be scanned or imaged in full or in part by the inspect device 210. Such imaging may occur after the container has been lifted out of its puck by a robotic arm, picker, or the like, or may be otherwise scanned or imaged while retained in the puck. In some embodiments, images and/or video captured by the inspect device 210 may be stored in the storage device 110 as a portion of the order data 118.

The unit of use device 212 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, liquids in a spray or other dispensing container, and the like. Prescription drug products dispensed by the unit of use device 212 may be packaged individually or collectively for shipping, or may be shipped in combination with other prescription drugs dispensed by other devices (e.g., in the high volume fulfillment center).

At least some of the operations of devices 206-232 may be directed by the order processing device 114. For example, the manual fulfillment device 216, the review device 218, the automated dispensing device 214, the packing device 226, and/or another device may receive instructions provided by the order processing device 114.

The automated dispensing device 214 may include one or more than one device that dispenses prescription drugs or pharmaceuticals into prescription containers in accordance with one or multiple prescription orders. In general, the automated dispensing device 214 may include mechanical and electronic components with, in some embodiments, software and/or logic to facilitate pharmaceutical dispensing that would otherwise be performed in a manual fashion by a pharmacist and/or pharmacist technician. For example, the automated dispensing device 214 may include high volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high volume fulfillment center.

The manual fulfillment device 216 may provide for manual fulfillment of prescriptions. For example, the manual fulfillment device 216 may receive or obtain a container and enable fulfillment of the container by a pharmacist or pharmacy technician. In some embodiments, the manual fulfillment device 216 provides the filled container to another device in the pharmacy fulfillment devices 112 to be joined with other containers in a prescription order for a patient or member. In general, a manual fulfillment may include operations at least partially performed by a pharmacist or a pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter). Prescription drugs dispensed by the manual fulfillment device 216 may be packaged individually or collectively for shipping, or may be shipped in combination with other prescription drugs dispensed by other devices in the high volume fulfillment center.

The review device 218 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like. In an example embodiment, the manual review may be performed at the manual station.

The imaging device 220 may image containers prior to filling and/or after they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114, and/or stored in the storage device 110 as part of the order data 118.

The cap device 222 may be used to cap or otherwise seal a prescription container. In some embodiments, the cap device 222 may secure a prescription container with a type of cap in accordance with a patient preference (e.g., a preference regarding child resistance, a preference regarding built-in adherence functionality, or the like), a plan sponsor preference, a prescriber preference, or the like. The cap device 222 may also etch a message into the cap, although this process may be performed by a different device in the high volume fulfillment center. The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218, at the high volume fulfillment center. The accumulation device 224 may be used to group the prescription containers prior to shipment to the member or otherwise.

The literature device 228 prints, or otherwise generates, literature to include with prescription drug orders. The literature may be printed on multiple sheets of substrates, such as paper, coated paper, printable polymers, or combinations thereof. The literature printed by the literature device 228 may include information required to accompany the prescription drugs included in a prescription order, relating to prescription drugs in the order, financial information associated with the order (e.g., an invoice or an account statement, or the like).

In some embodiments, the literature device 228 folds or otherwise prepares the literature for inclusion with a prescription drug order (e.g., in a shipping container). In some embodiments, the literature device 228 that prints the literature may be separate from the literature device that prepares the literature for inclusion with a prescription order.

The packing device 226 packages a prescription order in preparation for shipping the order. The packing device 226 may box, bag, or otherwise package the fulfilled prescription order for delivery. The packing device 226 may further place inserts (e.g., literature or other papers) into the packaging received from the literature device 228 or otherwise. For example, bulk prescription orders may be shipped in a box, while other prescription orders may be shipped in a bag which may be a wrap seal bag. The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, sort by zip code, or the like). The packing device 226 may include ice or temperature sensitive elements for prescriptions which are to be kept within a temperature range during shipping in order to retain efficacy or otherwise. The ultimate package may then be shipped through postal mail, through a mail order delivery service that ships via ground and/or air (e.g., UPS, FEDEX, DHL, or the like), through delivery service, through a locker box at a shipping site (e.g., AMAZON locker, a PO Box, or the like), or otherwise.

The unit of use packing device 230 packages a unit of use prescription order in preparation for shipping the order. The unit of use packing device 230 may include manual scanning of containers to be bagged for shipping to verify each container in the order. In an example embodiment, the manual scanning may be performed at a manual station.

The mail manifest device 232 receives packaged prescription orders, such as packaged prescription orders from packing device 142, unit of use packing device 144, or from elsewhere in the system 100. The mail manifest device 232 may sort and aggregate packaged prescription orders by geographic destination, grouping orders with other orders of like destinations. Geographically grouped orders may then be provided to shippers, such as the postal mail, a mail order delivery service that ships via group and/or air (e.g., UPS, FEDEX, or DHL), through another delivery service, through a locker box at a shipping site (e.g., AMAZON locker or a PO Box), or otherwise.

While the pharmacy fulfillment device 112 in FIG. 2 is shown to include single devices 206-232, multiple devices may be used. The devices 206-232 may be the same type or model of device or may be different device types or models. When multiple devices are present, the multiple devices may be of the same device type or models or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (e.g. by conveyors), networked, and/or otherwise in contact with one another or integrated with one another, (e.g., at the high volume fulfillment center). In addition, the functionality of a device may be split among a number of discrete devices and/or combined with other devices.

Figure 3:
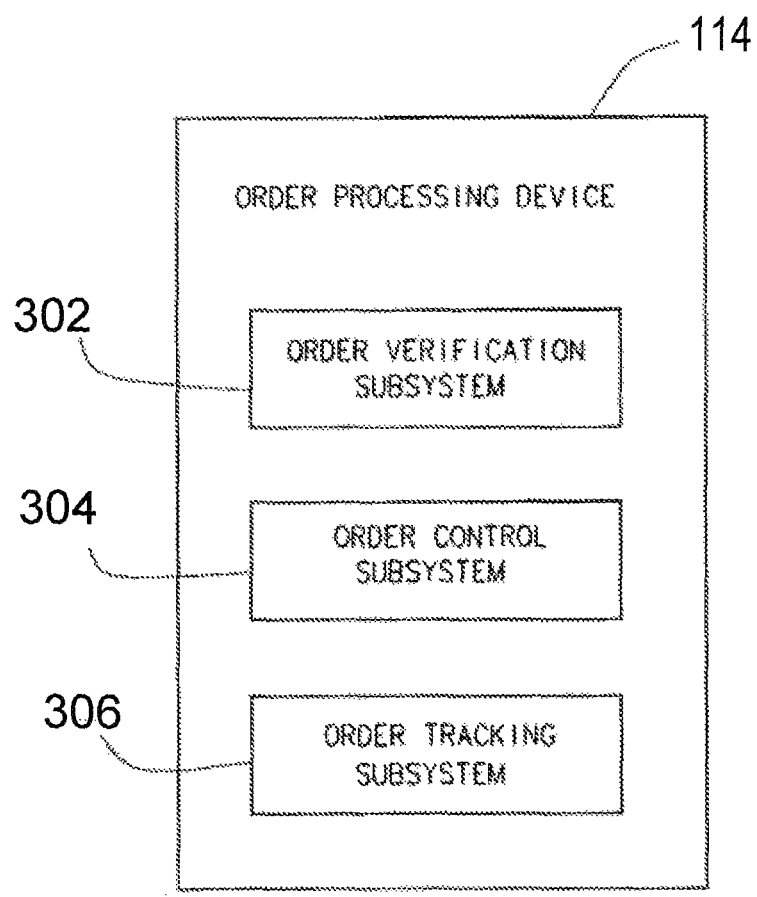
FIG. 3 is a block diagram of an example order processing device that may be deployed within the system of FIG. 1, according to an example embodiment.

FIG. 3 illustrates the order processing device 114, according to an example embodiment. The order processing device 114 may be used by one or more than one operators to generate prescription orders, make routing decisions, make prescription order consolidation decisions, track literature with the system 100, and/or view order status and other order related information. For example, the prescription order may consist of order components. The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to, verify the eligibility of the member, and review the formulary to determine appropriate copayment, coinsurance, and deductible for the prescription drug, and/or perform a DUR. Other communications between the order verification subsystem 302 and the benefit manager device 102 may be performed for a variety of purposes.

The order control subsystem 304 controls various movements of the containers and/or pallets along with various filling functions during their progression through the system 100. In some embodiments, the order control subsystem 304 may identify the prescribed drug in one or more than one prescription orders as capable of being fulfilled by the automated dispensing device 214. The order control subsystem 304 may determine which prescriptions are to be launched, and may determine that a pallet of automated-fill containers is to be launched. The order control subsystem 304 may determine that an automated-fill prescription of a specific pharmaceutical is to be launched, and may examine a queue of orders awaiting fulfillment for other prescription orders which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors to deliver the pallet from the loading device 208 to the manual fulfillment device 216, for example, from the literature device 228 to deliver paperwork as needed to fill the prescription.

The order tracking subsystem 306 may track a prescription order as it progresses (or stops) toward fulfillment. The order tracking subsystem 306 may track, record and/or update order history, order status, or the like. The order tracking subsystem 306 may store data locally (e.g., in a memory, etc.) or as a portion of the order data 118 stored in the storage 110.

Figure 4:
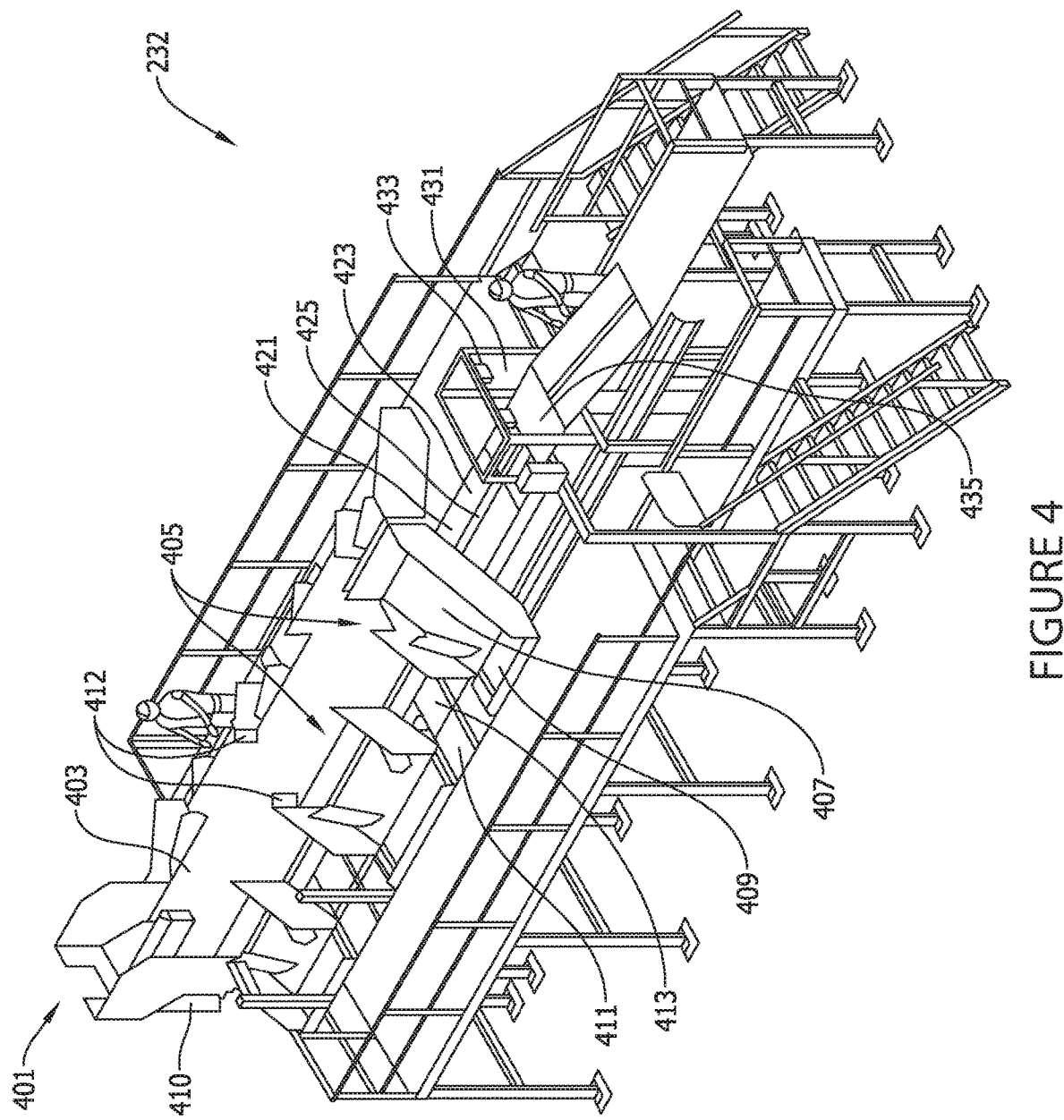
FIG. 4 is a perspective view of a mail manifest device, according to an example embodiment.

FIG. 4 illustrates a perspective view of an example mail manifest device 232, according to an example embodiment. The mail manifest device 232 enables sorting and aggregation of packaged prescription orders, such as by destination zip code or geography.

Figure 5:
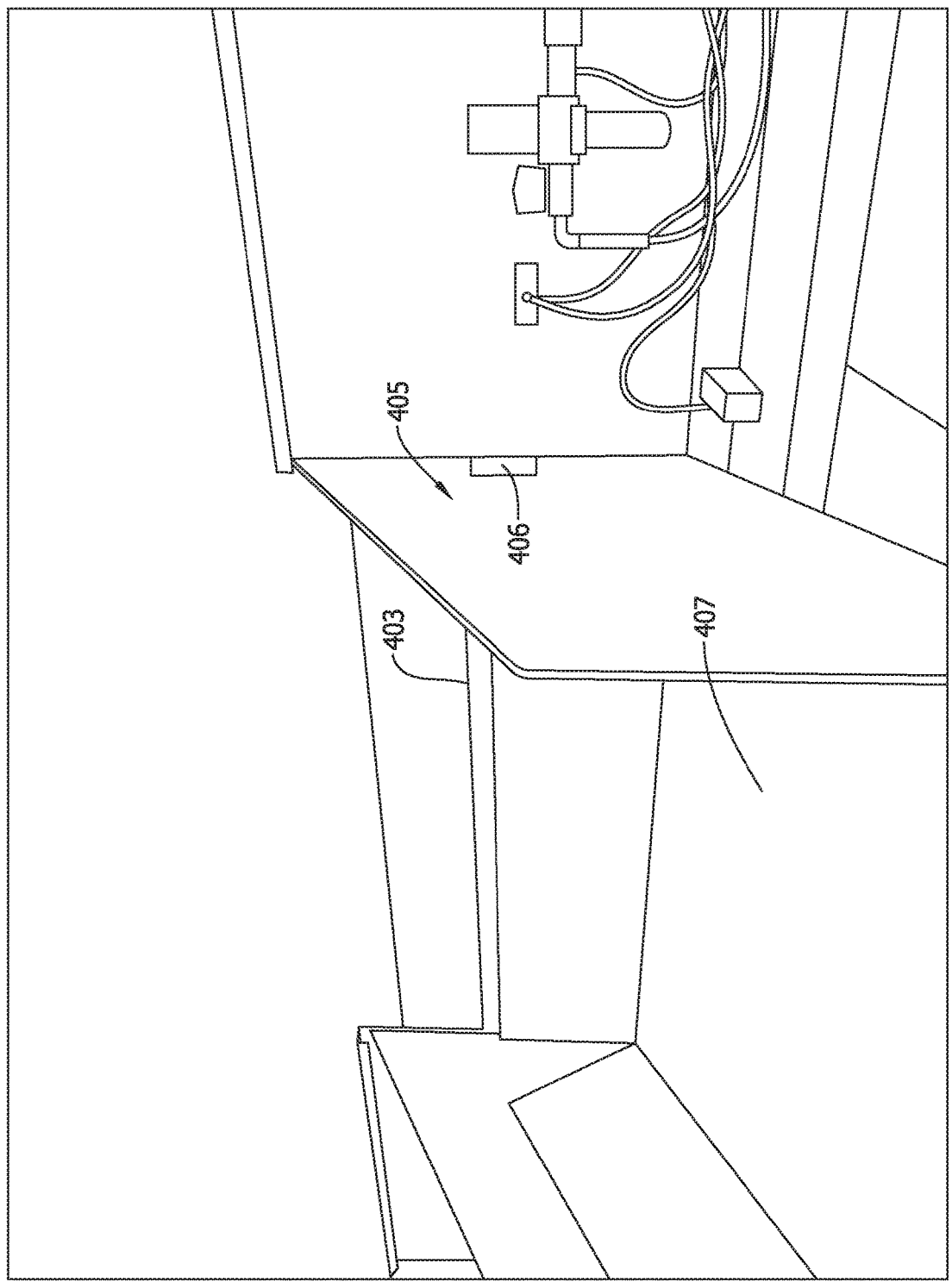
FIG. 5 is a perspective view of an inflow conveyor and slide of an mail manifest device, according to an example embodiment.

As shown in FIG. 4, the mail manifest device 232 may include an inflow section 401, which includes one or more inflow conveyors 403. Packaged prescription orders may be brought into the mail manifest device 232 from the packing device 226 and/or the unit of use packing device 230 via the inflow conveyor 403. The inflow conveyor 403 may be an Intralox® conveyor in an example embodiment. Orders may be transported by the inflow conveyor 403 to a station 405. In some embodiments, the mail manifest device 232 includes a single station 405. In some embodiments, the mail manifest device 232 includes multiple stations 405. Each station 405 may include a ramp or slide 407 leading down from the inflow conveyor 403 to a table 409. FIG. 5 illustrates a perspective view of an example slide 407 extending from an inflow conveyor 403.

Referring back to FIG. 4, a control device 410 may be embodied as a part of the order processing device 114 in an embodiment (see FIG. 8), and may cause one or more than one actuators 412 to direct a packaged order from the inflow conveyor 403 down the slide 407 of a station 405 and to the table 409 of the station 405 based on the capacity of each station 405. For example, a level sensor 406 (best seen in FIG. 5) may detect the volume of packaged orders already present at each station 405, and the control device 410 may cause the one or more than one actuators 412 to direct the next packaged order to the station 405 with the lowest volume. In an example embodiment, level sensor 406 may be a reflective banner sensor.

Figure 6:
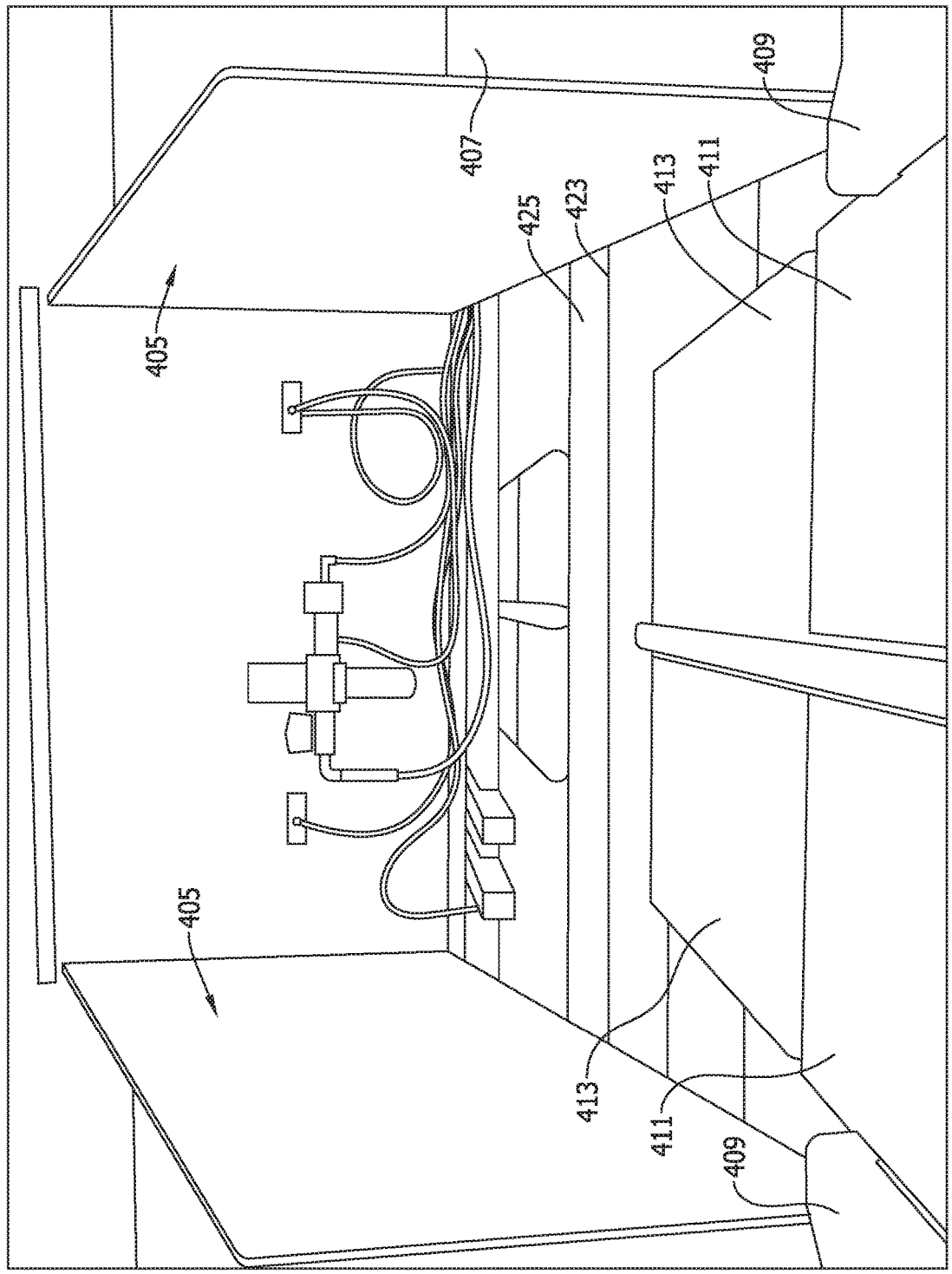
FIG. 6 is a perspective view of an example injection conveyor and staging conveyor of a mail manifest device, according to an example embodiment.

Once the packaged order is positioned on the table 409 of the station 405, the packaged order may be placed onto a staging conveyor 411. FIG. 6 illustrates a perspective view of an example station 405 including a staging conveyor 411. An operator may place the packaged order onto the staging conveyor 411 in an embodiment. In other embodiments, the packaged order may be placed on the staging conveyor 411 by other mechanics, such as by a robot or the like. The packaged order may include at least one identifier, which in an embodiment may be a two-dimensional barcode or other indicia which has been printed on, laser etched on, labeled on, or otherwise affixed to or apart of the packaging of the packaged order. In some embodiments, multiple identifiers may be included on the packaged order. The packaged order may be oriented on the staging conveyor 411, and in some embodiments may be oriented flat on the staging conveyor 411 so that at least one identifier is facing upwardly and is visible from overhead. The staging conveyor 411 may be any standard conveyor. In some embodiments, the staging conveyor is not continuous but actuates when the sensor senses a package within its field of view.

The staging conveyor 411 may advance the packaged order onto an injection conveyor 413 when a sensor 426 detects that the injection conveyor 413 is empty. In general, the injection conveyor 413 may differ from a standard conveyor in that standard conveyors are generally designed to be in continuous or near-continuous use. The injection conveyor 413 may be designed for use in short, high intensity intervals with rapid acceleration and deceleration, thereby injecting the packaged order to another location rapidly. In an example embodiment, the injection conveyor 413 may include a motor capable of rapid acceleration and deceleration, and/or a conveyor belt made of a material with a sufficiently high coefficient of friction (such as plastic, rubber or the like). In an embodiment, the injection conveyor 413 may inject the packaged order into an outflow section 421 of the mail manifest device 232.

Figure 7:
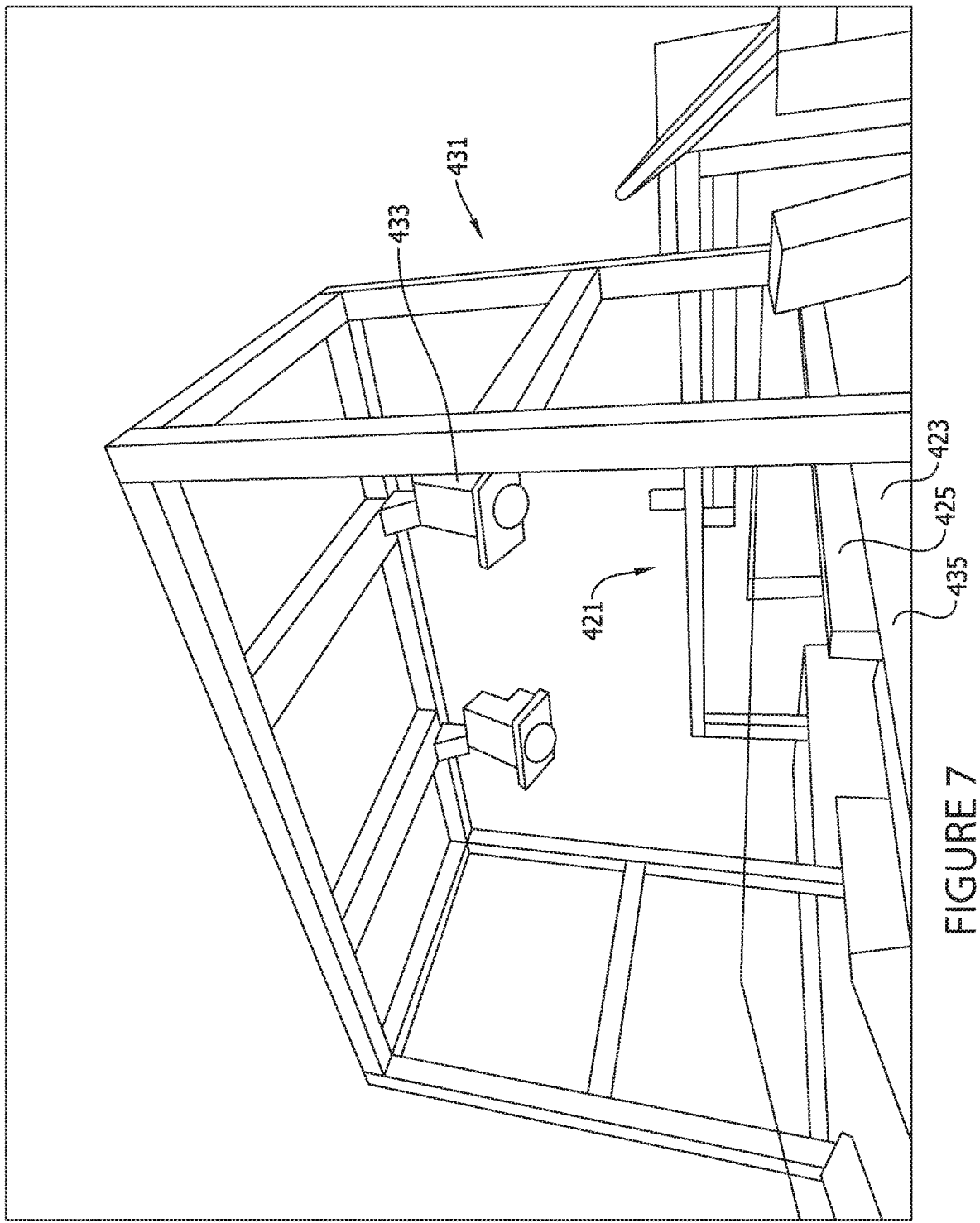
FIG. 7 is a perspective view of an camera system of a mail manifest device, according to an example embodiment.

FIG. 7 illustrates a perspective view of an outflow section 421 according to an example embodiment. The outflow section 421 may include one or more than one outflow conveyors 423 and a center divider 425. One or more than one outflow conveyor 423 may be a cleated conveyor for moving a packaged order away from an injection conveyor 413. In an example embodiment, another outflow conveyor 423 may be a scale conveyor that may weigh the packaged order. The cleated outflow conveyor may deliver packaged orders to the scale conveyor to be weighed. In another example embodiment, another outflow conveyor 423 may be a camera or scanner conveyor on which the packaged order may be imaged and/or scanned. The scale conveyor may deliver packaged orders to the camera conveyor. However, a single outflow conveyor 423 may be used instead of a separate cleated conveyor, scale conveyor, and camera conveyor.

In an embodiment, two outflow conveyors 423 may be provided, with the center divider 425 positioned there between. The outflow conveyor 423 may be, for example, a cleated conveyor in an embodiment. The outflow section 421 may be positioned below the inflow section 401 as shown in FIG. 4, however other orientations and positioning may be used in some embodiments.

In operation, when an open slot is detected on the outflow conveyor 423 (such as via the sensor 426), the injection conveyor 413 accelerates to inject the packaged order into the open slot on the outflow conveyor 423. In an example embodiment, the injection conveyor 413 may be oriented approximately perpendicular to the outflow conveyor 423, thereby injecting packaged orders at approximately ninety degrees onto the outflow conveyor 423. Due to the relatively high rate of speed at which the packaged order is injected onto the outflow conveyor 423, for example, the center divider 425 may act as a backstop to prevent the packaged order from overshooting the outflow conveyor 423. The center divider 425 arranged between the two sides of the outflow conveyors 423 removes spaces between the outflow conveyors 423 and further increases the volume of packaged orders to be injected and the injecting speed. The injection conveyor 413 and the center divider 425 allow for reliable injection of packaged orders at ninety degree or near-ninety degree angles onto the outflow conveyor 423, without the orientation and/or positioning of the package becoming unsuitable for later scanning and tracking.

As shown in FIGS. 4 and 7, the outflow conveyor 423 may transport the injected packaged order to a camera system 431 in an example embodiment. The camera system 431 may include one or more than one cameras 433, which may be, for example, a Cognex camera model DMR-503X. In some embodiments, the camera 433 is capable of at least 120 decodes per second and at least 150 frames per second of the packaged order at a resolution of at least 2048×1088 pixels. In an example embodiment, at least twelve images of a passing packaged order may be captured by the at least one camera 433. As such, the one or more than one camera used herein provide the ability to scan/read massive packaged orders within a very short time. Using the captured images of the packaged order, the control device 410 may confirm the identity of the packaged order via the at least one identifier. Additionally, the camera system 431 may include a scale 435 for weighing each packaged order. A single scale 435 or multiple scales 435 may be included in the mail manifest device 232.

Figure 8:
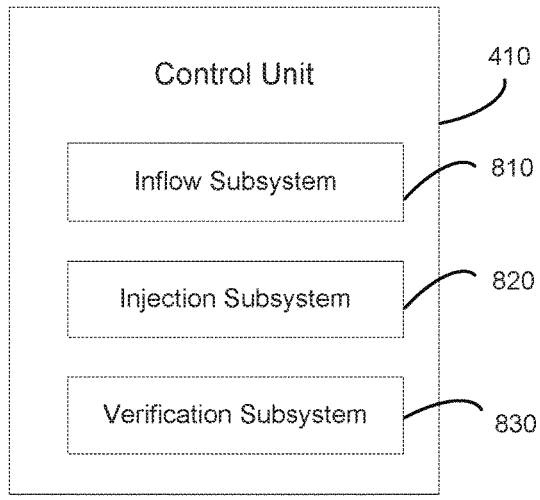
FIG. 8 is a block diagram of an control device of a mail manifest device, according to an example embodiment.

FIG. 8 illustrates the control device 410, according to an example embodiment. The control device 410 may be deployed in the mail manifest device 232 as reflected in FIG. 4, or may otherwise be deployed. In some embodiments, the control device 410 directs operations being performed by elements of the mail manifest device 232 as shown in FIGS. 4-7.

The control device 410 may include an inflow subsystem 810, an injection subsystem 820, and a verification subsystem 830. Each subsystem may include circuitry (e.g., processors), logic, and memory, to execute instructions on sensed data. The control device 410 may be responsible for directing packaged orders to selected stations 405, and routing packaged orders after being verified via imaging and weighing by the camera system 431. For example, the control device 410 may be communicatively coupled to various sensors (collectively numbered 426 herein), the actuators 412, the injection conveyor 413, the camera system 431, and the like.

The inflow subsystem 810 may enable the control device 410 to direct incoming packaged orders to stations 405 based on the volume of packaged orders already being handled by each station 405. The injection subsystem 820 may monitor the sensors 426 within the outflow section 421 to determine when an opening exists on the outflow conveyor 423. The injection subsystem 820 may further control the staging conveyor 411 and the injection conveyor 413 to inject a packaged order onto the outflow conveyor 423 at the detected opening. The verification subsystem 830 may communicate with the camera system 431 to image and weigh the packaged order coming off of the outflow conveyor 423. For example, the verification subsystem 830 may further communicate with the storage device 110 to verify the imaged and weight information obtained from the camera system 431, and may thereafter route each packaged order for accumulation by destination locations.

Figure 9:
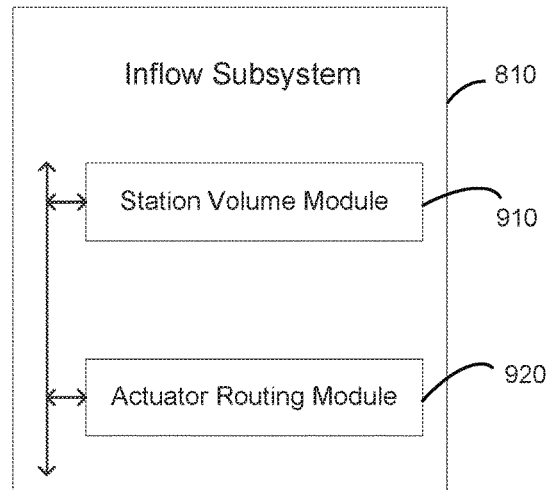
FIG. 9 is a block diagram of an inflow subsystem of a mail manifest device, according to an example embodiment.

FIG. 9 illustrates an example inflow subsystem 810 that may be deployed in the control device 410, or may be otherwise deployed in another system. One or more than one modules are communicatively coupled and included in the inflow subsystem 810 to enable the inflow subsystem 810 to control flow of incoming packaged orders. The modules of the inflow subsystem 810 that may be included are a station volume module 910 and an actuator routing module 920. Other modules may also be included. Each module may include circuitry (e.g., processors), logic, and memory, to execute instructions on sensed data or calculated data.

In some embodiments, the modules of the inflow subsystem 810 may be distributed so that some of the modules are deployed in other devices within the pharmacy. In one embodiment, the modules are deployed in memory and executed by a processor coupled to the memory. The functionality contained within the modules 910, 920 may be combined into a lesser number of modules, further divided among a greater number of modules, or redistributed among existing modules. Other configurations including the functionality of the modules 910,920 may be used.

The station volume module 910 may communicate with one or more than one of the sensors 426, which may be level sensors that detect the current volume at each station 405 in an example embodiment. In some embodiments, the station volume module 910 may determine the volume of packaged orders at each station 405 merely by tracking the number of packaged orders already routed to each station 405 as compared to the number of packaged orders leaving each station 405. For example, the station volume module 910 may determine which station 405 has the lowest volume. In some embodiments, other criterion may be used to select a station 405 to which a packaged order is to be directed. The actuator routing module 920 may then cause the actuators 412 to direct the packaged order on the inflow conveyor 403 to the selected station 405. For example, the actuators 412 may be pneumatic, electric, or otherwise in operation, and may be selectively moveable to selectively channel the packaged order to the selected station 405.

Figure 10:
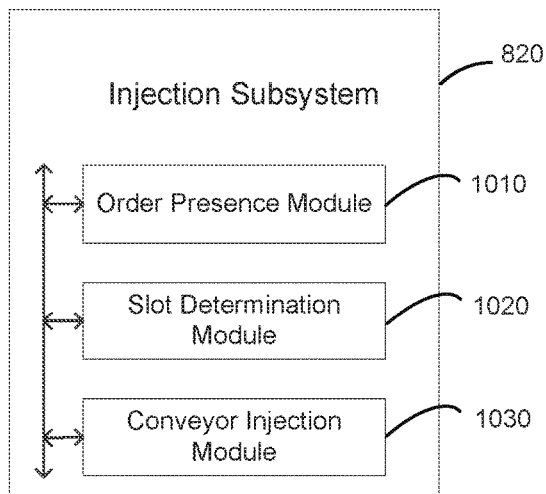
FIG. 10 is a block diagram of an injection subsystem of a mail manifest device, according to an example embodiment.

FIG. 10 illustrates an example injection subsystem 820 that may be deployed in the control device 410, or may be otherwise deployed in another system. One or more than one modules are communicatively coupled and included in the injection subsystem 820. Each module may include circuitry (e.g., processors), logic, and memory, to execute instructions on sensed data or calculated data. The modules of the injection subsystem 820 that may be included are an order presence module 1010, a slot determination module 1020, and a conveyor injection module 1030. Other modules may also be included.

In some embodiments, the modules of the injection subsystem 820 may be distributed so that some of the modules are deployed in other devices within the pharmacy. In one embodiment, the modules are deployed in memory and executed by a processor coupled to the memory. The functionality contained within the modules 1010-1030 may be combined into a lesser number of modules, further divided among a greater number of modules, or redistributed among existing modules. Other configurations including the functionality of the modules 1010-1030 may be used.

The order presence module 1010 may be in communication with one or more than one of the sensors 426 to monitor for the presence of a packaged order on the injection conveyor 413. When there is no packaged order on the injection conveyor 413, the order presence module 1010 may cause the staging conveyor 411 to engage, thereby advancing the packaged order from the staging conveyor 411 to the injection conveyor 413. The staging conveyor 411 may remain in motion until a packaged order is detected on the injection conveyor 413, or may remain still until a packaged order is placed thereon and the injection conveyor 413 is determined to be empty. The slot determination module 1020 may be in communication with the one or more than one sensors 426 for determining whether an empty slot exists on the outflow conveyor 423. Upon determining that an empty slot exists on the outflow conveyor 423, the conveyor injection module 1030 may control the injection conveyor 413 to accelerate rapidly, thereby injecting the packaged order onto the outflow conveyor 423 into the open slot thereon. For example, the injection conveyor 413 may operable to accelerate from still to approximately 10.4 inch per second in approximately 1 second.

Figure 11:
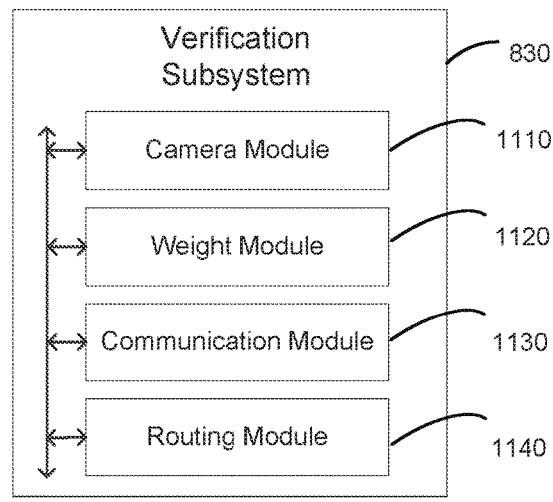
FIG. 11 is a block diagram of an verification subsystem of a mail manifest device, according to an example embodiment.

FIG. 11 illustrates an example verification subsystem 830 that may be deployed in the control device 410, or may be otherwise deployed in another system. One or more than one modules are communicatively coupled and included in the verification subsystem 830. Each module may include circuitry (e.g., processors), logic, and memory, to execute instructions on sensed data or calculated data. The modules of the verification subsystem 830 that may be included are a camera module 1110, a weight module 1120, a communication module 1130, and/or a routing module 1140. Other modules may also be included.

In some embodiments, the modules of the verification subsystem 830 may be distributed so that some of the modules are deployed in other devices within the pharmacy. In one embodiment, the modules are deployed in memory and executed by a processor coupled to the memory. The functionality contained within the modules 1110-1140 may be combined into a lesser number of modules, further divided among a greater number of modules, or redistributed among existing modules. Other configurations including the functionality of the modules 1110-1140 may be used.

The camera module 1110 may be in communication with the one or more than one cameras 433 of the camera system 431. The camera module 1110 may cause the cameras 433 to image a packaged order as it passes by the camera system 431. In an example embodiment, the camera module 1110 may cause the one or more cameras 433 to image a passing packaged order at a rate of 150 frames/second and 120 decodes/second. The weight module 1120 may communicate with the scale 435 of the camera system 431 to determine the weight of a passing packaged order. In some embodiments, the packaged order may pause as it is weighed, although in other embodiments the packaged order may be weighed by the scale 435 while still in motion. The communication module 1130 may be in communication with, for example, the storage device 110, the camera module 1110, and the weight module 1120. Thereby, the communication module 1130 may receive the weight of the passing packaged order and at least one image of the packaged order, and may communicate with the storage device 110 to access order data 118, member data 120, claims data 122, drug data 124, prescription data 126, as desired for confirming the identity of the packaged order.

In an example embodiment, if the packaged order is identified by the image identifier thereon as containing one or more than one prescription orders that should be a certain weight, and if the weight from the scale 435 sufficiently differs from the expected weight (e.g., beyond a predetermined threshold), the routing module 1140 may cause the packaged order to be routed for further verification. However, when the weight of the packaged order is within tolerances of the expected weight, the routing module 1140 may control a routing device to route the packaged order to an accumulation area with other packaged orders to be shipped (e.g., to the same general geographic area). In an example embodiment, a routing device may have similar functionality to the inflow section 401, in which the routing module 1140 may control one or more than one actuators to direct the packaged order from a conveyor to the accumulation area. In an another embodiment, packaged orders may be sorted in a pharmacy rather than being routed to an accumulation area.

In some embodiments, the use of smaller weight tolerances may result in more false positives. For example, a tighter tolerance range could be used to monitor for a missing dose of a pharmaceutical, but would likely result in more false positives due to normal variances in weights of various objects in the order. In some embodiments, the tolerance may be less than the weight of a single prescription order, so as to monitor for a missing bottle of pills.

Figure 12:
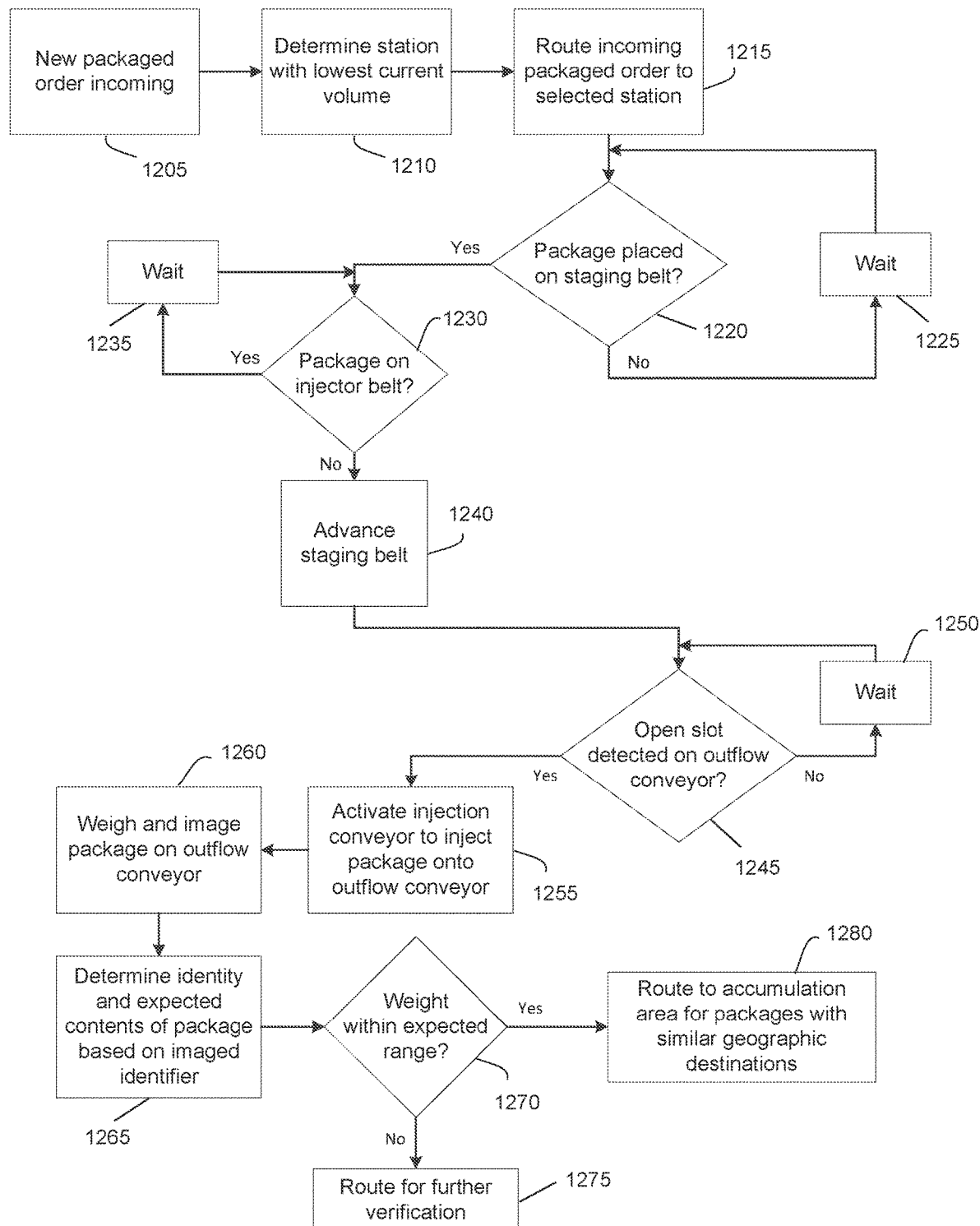
FIG. 12 is an process flow illustrating a method for mail manifest, according to an example embodiment.

FIG. 12 illustrates a method 1200 for sorting packaged orders for shipment, according to an example embodiment. The method 1200 may be performed by the mail manifest device 232 (e.g., as instructed by the control device 410), or may be otherwise performed.

At block 1205, a new packaged order comes into the mail manifest device 232 via the inflow conveyor 403. At block 1210, a determination is made as to which station 405 has the lowest volume. At block 1215, the packaged order is routed to the selection station 405 by the actuators 412.

At decision point 1220, a determination is made as to whether a packaged order has been placed on the staging conveyor 411. When no packaged order is detected on the staging conveyor 411, the method 1200 waits at block 1225 until a packaged order is detected thereon. Once a packaged order is detected on the staging conveyor, at decision point 1230, a determination is made regarding whether a packaged order is already present on the associated injection conveyor 413. When a packaged order is detected on the injection conveyor 413, the method 1200 waits at block 1235 until a packaged order is no longer detected thereon. Once a packaged order is no longer detected on the injection conveyor 413, at block 1240 the staging conveyor 411 is advanced and the packaged order thereon is moved onto the injection conveyor 413. At decision point 1245, a determination is made as to whether an open slot exists on the outflow conveyor 423. When an open slot is not detected on the outflow conveyor 423, the method 1200 waits at block 1250 until an open slot is detected thereon. Once an open slot is detected on the outflow conveyor 423, at block 1255 the injection conveyor 413 is activated to inject the packaged order thereon onto the outflow conveyor 423 in the detected open slot.

At block 1260, the packaged order is weighed by the scale 435, and is imaged by at least one of the one or more than one cameras 433. At block 1265, a determination is made as to the identity an expected contents of the packaged order based on the imaged identifier thereon. At decision point 1270, a determination is made as to whether the weight of the packaged order is within an expected range based on information about the intended contents of the packaged order. In an example embodiment, the expected weight range of the packaged order may include the weight of intended pharmaceuticals, packaging materials, instructional materials, and the like. If the weight of the packaged order is outside of the expected weight range, at block 1275 the packaged order is routed for further verification within the pharmacy. If the weight of the packaged order is within the expected weight range, at block 1280 the packaged order is routed to an accumulation area for packages (e.g., with similar geographic destinations). Other criterion for accumulating packaged orders may also be used in other embodiments.

The mail manifest device 232 as described above may be deployed in the system 100 or otherwise deployed. Other types of and/or variations of the mail manifest device 232 may also be deployed.

Figure 13:
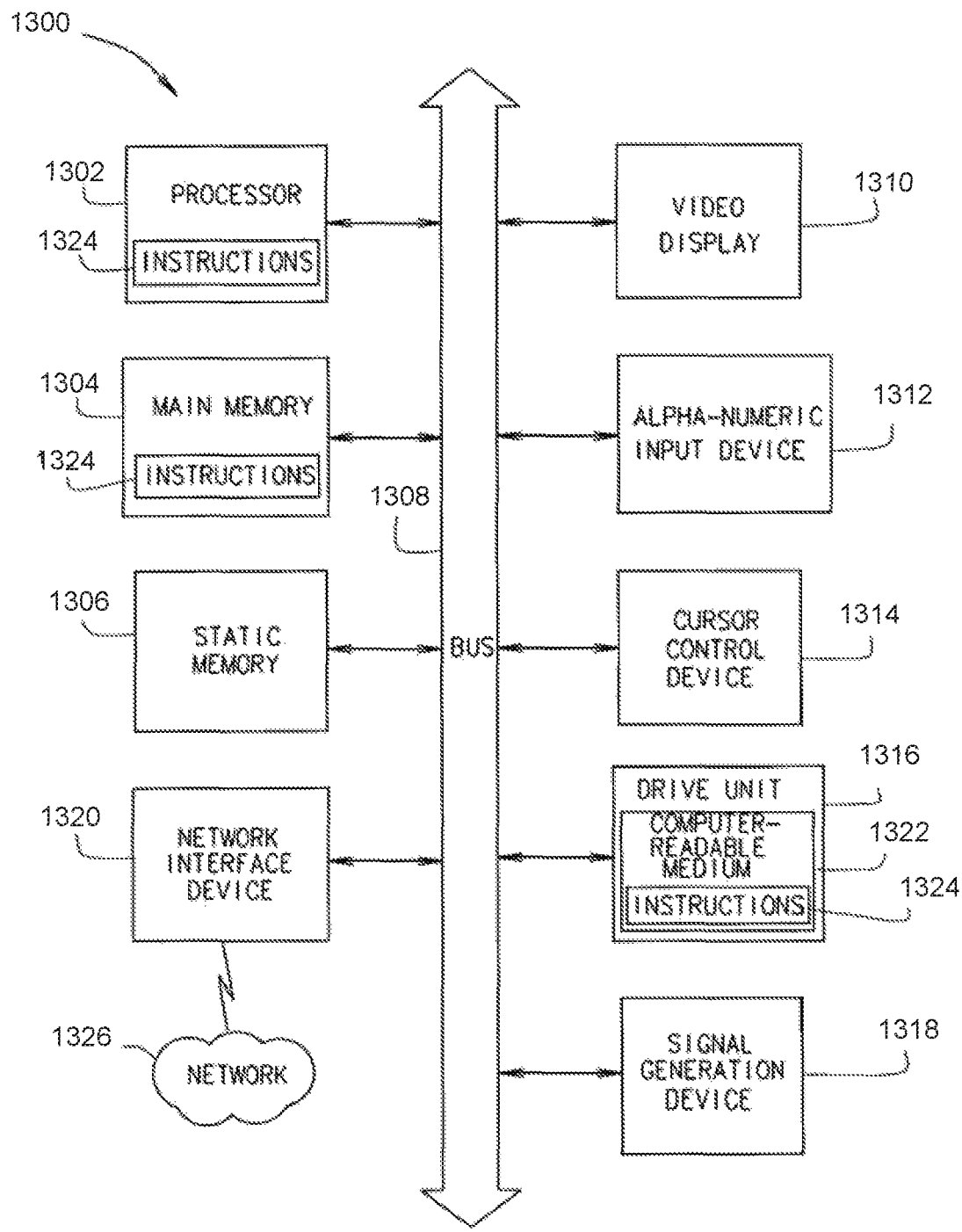
FIG. 13 is a block diagram of a machine in the example form of a computer system within which a set of processor-executable instructions for causing the machine to perform any one or more than one methodologies discussed herein may be executed or stored.

FIG. 13 shows a block diagram of a mail manifest in the example form of a computer system 1300 within which a set of instructions may be executed causing the machine to perform any one or more than one methods, processes, operations, or methodologies discussed herein. The devices 206-232, for example, may include the functionality of the one or more than one computer systems 1300. These devices and systems are dedicated to performing any one or more than one methods, processes, operations, or methodologies discussed herein.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The example computer system 1300 includes a processor 1302 (e.g., a central processing unit (CPU), a graphics processing unit (GPU) or both, etc.), a main memory 1304 and a static memory 1306, which communicate with each other via a bus 1308. The computer system 1300 further includes a video display unit 1410 (e.g., a liquid crystal display (LCD) or a cathode ray tube (CRT), etc.). The computer system 1300 also includes an alphanumeric input device 1412 (e.g., a keyboard, etc.), a cursor control device 1314 (e.g., a mouse, etc.), a drive unit 1316, a signal generation device 1318 (e.g., a speaker, etc.) and a network interface device 1320.

The drive unit 1316 includes a computer readable medium 1322 on which is stored one or more than one sets of instructions (e.g., software 1324, etc.) embodying any one or more than one methodologies or functions described herein. The instructions 1324 may also reside, completely or at least partially, within the main memory 1304 and/or within the processor 1302 during execution thereof by the computer system 1300, the main memory 1304 and the processor 1302 also constituting non-transitory computer readable media. When loaded with the instructions 1324, the processor 1302 is a machine dedicated to only the present processes and methodologies.

The instructions 1324 may further be transmitted or received over a network 1326 via the network interface device 1320.

While the computer-readable medium 1322 is shown in an example embodiment to be a single medium, the term "computer-readable medium" should be taken to include a single medium or multiple media (e.g., a centralized or distributed database, and/or associated caches and servers, etc.) that store the one or more than one sets of instructions. The term "computer-readable medium" shall also be taken to include any medium that is capable of storing or encoding a set of instructions for execution by the machine and that cause the machine to perform any one or more than one methodologies of the present invention. The term "Computer-readable medium" shall accordingly be taken to include, but not be limited to, solid-state memories, and optical media, and magnetic media. In some embodiments, the computer-readable medium is a non-transitory computer-readable medium. In other examples, a computer-readable medium is any medium that satisfies statutory requirements and stores instructions for use by a machine.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The embodiments of the present disclosure generally provide for a plurality of circuits or other electrical devices, which can be used in units, modules, systems, and sub-systems and the like. All references to such and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical/operational implementation that is desired. It is recognized that any circuit or other electrical device disclosed herein may include any number of microprocessors, discrete circuit components, integrated circuits, memory devices (e.g., FLASH, random access memory (RAM), read only memory (ROM), electrically programmable read only memory (EPROM), electrically erasable programmable read only memory (EEPROM), or other suitable variants thereof, etc.) and instructions (e.g., software, etc.) which co-act with one another to perform operation(s) disclosed herein. In addition, any one or more than one electric devices may be configured to execute a computer-program that is embodied in a computer readable medium that is programmed to perform any number of the functions and features as disclosed. The computer readable medium may be non-transitory or in any form readable by a machine or electrical component.

The inventive subject matter may be represented in a variety of different embodiments of which there are many possible permutations.

The present disclosure makes reference to a robot and words of similar import. A robot can be a machine capable of carrying out a complex series of actions automatically. These complex series of actions may include picking up, orientating, positioning and/or releasing a prescription component, a pill, a container or other structure. The robot may be dedicated to a single series of movements or may be able to execute multiple series of movements. A robot may include a processor that received instructions and then executes instructions to control its movement. In another example, a robot may resemble a human being and replicate certain human movements and functions, may move location, have an articulated arm, have grasping structures that replicate fingers and do not damage containers, and the like.

In an example embodiment, a system can include an outflow conveyor, and an injection conveyor to inject a package located thereon onto the outflow conveyor. The injection conveyor can be adjacent to the outflow conveyor and oriented substantially perpendicular to the outflow conveyor. The system can also include a monitoring system positioned to perform package monitoring of the outflow conveyor and to image the package on the outflow conveyor after the package has been injected onto the outflow conveyor. The monitoring system can be further configured to determine an intended destination of the package based on an identifier detected on the package in the image captured by the monitoring system. A routing device can be positioned to perform package routing of the package to an accumulation area for packages based on the determination of the intended destination of the package.

In an example embodiment, a method can include engaging an injection conveyor to inject a package located thereon onto an outflow conveyor. The injection conveyor can be oriented substantially perpendicular to the outflow conveyor. An image of the package on the outflow conveyor may be captured, and an identifier on the package may be detected from the image. An intended destination for the package may be determined based on the identifier, and the package may be routed to an accumulation area for packages intended for the intended destination.

Thus, methods and systems for a mail manifest have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more than one particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more than one operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

The invention claimed is:

1. A system comprising:
an inflow conveyor;
an outflow conveyor;
a staging conveyor;
a station positioned adjacent the staging conveyor;
an actuator coupled to the inflow conveyor, the actuator to direct a package from the inflow conveyor to the station for placement onto the staging conveyor; and
an injection conveyor to inject the package located thereon into an open slot on the outflow conveyor by accelerating the package from a still position, the package advanced onto the injection conveyor from the staging conveyor, the injection conveyor being adjacent to the outflow conveyor and oriented substantially perpendicular to the outflow conveyor.

2. The system of claim 1, wherein the station includes a ramp and a table, and wherein the actuator directs the package from the inflow conveyor down the ramp to the table.

3. The system of claim 1, further comprising:
an additional station positioned adjacent the staging conveyor;
a level sensor in communication with the injection conveyor to monitor package volume at the station and the additional station; and
an additional actuator coupled to the inflow conveyor, the additional actuator to direct an additional package from the inflow conveyor to the additional station for placement onto the staging conveyor based on monitoring of package volume at the station and the additional station.

4. The system of claim 3, wherein the level sensor is a banner level sensor.

5. The system of claim 3, further comprising:
a second station positioned adjacent a second staging conveyor; and
a control device in communication with the level sensor positioned to monitor a volume of additional packages at each of the first and second stations, the control device controlling the actuator to route the package to the station with a lowest volume of packages.

6. The system of claim 3, further comprising:
a second station positioned adjacent a second staging conveyor; and
a control device configured to count a number of packages at a first station and a number of additional packages at the second station, the control device controlling the actuator to route a subsequence package to one of the first station and the second station with a lower number of packages.

7. The system of claim 1, wherein the outflow conveyor is cleated.

8. The system of claim 1, wherein the outflow conveyor includes an imager to image the package on the outflow conveyor after the package has been injected onto the outflow conveyor and using the image to assist in determining an intended destination of the package.

9. The system of claim 1, wherein the outflow conveyor includes a backstop positioned opposite the injection conveyor as a package injection barrier.

10. The system of claim 1, further comprising:
a monitoring system including a scale to weigh an additional package, the monitoring system further configured to:
verify a weight of the additional package is within a predetermined amount from an expected weight of the additional package, and
flag the additional package as an exception when the weight of the additional package is not within the predetermined amount from the expected weight of the additional package.

11. The system of claim 10, wherein the monitoring system is further configured to:
access data regarding expected pharmaceutical contents in the package from a database based on an identifier on the package imaged by the monitoring system; and
determine the expected weight of the expected pharmaceutical contents and any additional materials within the package and the package.

12. A system comprising:
an inflow conveyor;
an outflow conveyor;
a staging conveyor;
a station positioned adjacent the staging conveyor;
a scanner at one of the outflow conveyor, the station, or both, the scanner to read an identifier on a package at one of the outflow conveyor, the station, or both to identify the package and an order;
an actuator coupled to the inflow conveyor, the actuator to direct the package from the inflow conveyor to the station for placement onto the staging conveyor; and
an injection conveyor to inject a package located thereon into an open slot on the outflow conveyor by accelerating the package from a still position, the package advanced onto the injection conveyor from the staging conveyor, the injection conveyor being adjacent to the outflow conveyor and oriented at an angle to the outflow conveyor.

13. The system of claim 12, wherein the outflow conveyor includes a scale conveyor, a camera conveyor, a cleated conveyor, or combinations thereof.

14. The system of claim 12, wherein the injection conveyor includes a belt comprised of plastic, rubber, or combinations thereof.

15. The system of claim 12, further comprising:
a monitoring system positioned to perform package monitoring of the outflow conveyor and to image the package on the outflow conveyor after the package has been injected onto the outflow conveyor, the monitoring system being further configured to determine an intended destination of the package based on the identifier detected on the package by the scanner; and
a routing device positioned to perform package routing of the package to a package accumulation area for based on the determination of the intended destination of the package.

16. The system of claim 15, wherein the monitoring system includes a scale to weigh an additional package, the monitoring system further configured to:
verify a weight of the additional package is within a predetermined amount from an expected weight of the additional package, and
flag the additional package as an exception when the weight of the additional package is not within the predetermined amount from the expected weight of the additional package.

17. The system of claim 16, wherein the monitoring system is further configured to:
access data regarding expected pharmaceutical contents and additional materials within the package from a database based on the identifier on the package imaged by the monitoring system; and
determine the expected weight of the expected pharmaceutical contents and the additional materials within the package and the package itself.

18. The system of claim 12, wherein the injection conveyor includes a conveyor belt made of a material having a coefficient of friction such that the injection conveyor may accelerate the package from still to approximately 10.4 inches per second in approximately one second.

19. The system of claim 12, wherein the outflow conveyor includes a center divider positioned opposite the injection conveyor, and wherein the center divider is configured to inhibit the package from overshooting the outflow conveyor when the injection conveyor injects the package into the open slot on the outflow conveyor.

20. The system of claim 19, further comprising a sensor positioned to monitor the outflow conveyor and in communication with the injection conveyor, wherein the sensor is configured to detect the open slot on the outflow conveyor.

* * * * *